United States Patent
Bailly

(10) Patent No.: US 10,405,960 B2
(45) Date of Patent: Sep. 10, 2019

(54) TEXTILE-BASED PROTHESIS FOR LAPAROSCOPIC SURGERY

(71) Applicant: Sofradim Production, Trévoux (FR)

(72) Inventor: Pierre Bailly, Caluire-et-Cuire (FR)

(73) Assignee: Sofradim Production, Trevoux (FR)

( * ) Notice: Subject to any disclaimer, the term of this patent is extended or adjusted under 35 U.S.C. 154(b) by 181 days.

(21) Appl. No.: 14/784,058

(22) PCT Filed: Jun. 5, 2014

(86) PCT No.: PCT/EP2014/061654
§ 371 (c)(1),
(2) Date: Oct. 13, 2015

(87) PCT Pub. No.: WO2014/195388
PCT Pub. Date: Dec. 11, 2014

(65) Prior Publication Data
US 2016/0051357 A1    Feb. 25, 2016

(30) Foreign Application Priority Data

Jun. 7, 2013 (FR) .................................... 13 55258

(51) Int. Cl.
*A61F 2/00* (2006.01)
*A61B 90/00* (2016.01)

(52) U.S. Cl.
CPC .... *A61F 2/0063* (2013.01); *A61B 2090/0816* (2016.02); *A61F 2002/0068* (2013.01); *A61F 2002/0072* (2013.01); *A61F 2210/0004* (2013.01); *A61F 2230/0008* (2013.01);
(Continued)

(58) Field of Classification Search
CPC .................................................... A61F 2/0063
See application file for complete search history.

(56) References Cited

U.S. PATENT DOCUMENTS

| 1,187,158 A | 6/1916 | Mcginley |
| 3,118,294 A | 1/1964 | Van Laethem |
| 3,124,136 A | 3/1964 | Usher |

(Continued)

FOREIGN PATENT DOCUMENTS

| CA | 1317836 C | 5/1993 |
| DE | 19544162 C1 | 4/1997 |

(Continued)

OTHER PUBLICATIONS

Ellouali, M. et al., "Antitumor Activity of Low Molecular Weight Fucans Extracted from Brown Seaweed Ascophyllum Nodosum," Anticancer Res., Nov.-Dec. 1993, pp. 2011-2020, 12 (6A).

(Continued)

*Primary Examiner* — Shaun L David

(57) ABSTRACT

The invention relates to a prosthesis (1) comprising a textile (2) of elongate shape defining a longitudinal axis A, and a resilient frame (3) connected to said textile along substantially the peripheral edge of the textile, said frame forming, in the area of each short side of the textile, at least one U-shaped bend (4) extending in the direction of the longitudinal axis, said frame being able to adopt an unstressed configuration, in which said textile is deployed, and a stressed configuration, in which said frame is subjected to a radial force directed towards said longitudinal axis and said textile forms at least one longitudinal fold.

20 Claims, 3 Drawing Sheets

Figure 1:
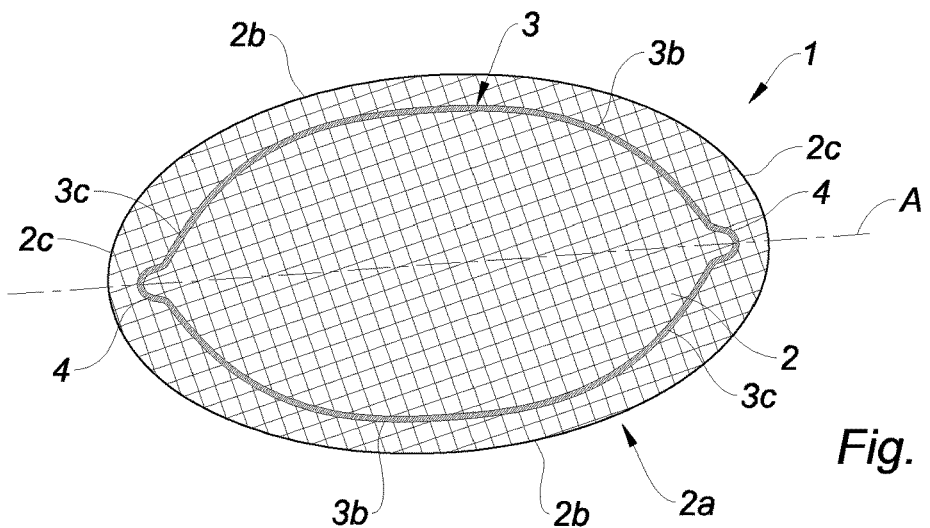

(52) U.S. Cl.
CPC .............. *A61F 2230/0019* (2013.01); *A61F 2250/0031* (2013.01)

(56) References Cited

U.S. PATENT DOCUMENTS

| | | |
|---|---|---|
| 3,272,204 A | 9/1966 | Charles et al. |
| 3,276,448 A | 10/1966 | Usher |
| 3,320,649 A | 5/1967 | Naimer |
| 3,364,200 A | 1/1968 | Ashton et al. |
| 3,570,482 A | 3/1971 | Emoto et al. |
| 4,006,747 A | 2/1977 | Kronenthal et al. |
| 4,060,081 A | 11/1977 | Yannas et al. |
| 4,173,131 A | 11/1979 | Pendergrass et al. |
| 4,193,137 A | 3/1980 | Heck |
| 4,248,064 A | 2/1981 | Odham |
| 4,294,241 A | 10/1981 | Miyata |
| 4,307,717 A | 12/1981 | Hymes et al. |
| 4,338,800 A | 7/1982 | Matsuda |
| 4,476,697 A | 10/1984 | Schafer et al. |
| 4,487,865 A | 12/1984 | Balazs et al. |
| 4,500,676 A | 2/1985 | Balazs et al. |
| 4,511,653 A | 4/1985 | Play et al. |
| 4,527,404 A | 7/1985 | Nakagaki et al. |
| 4,591,501 A | 5/1986 | Cioca |
| 4,597,762 A | 7/1986 | Walter et al. |
| 4,603,695 A | 8/1986 | Ikada et al. |
| 4,631,932 A | 12/1986 | Sommers |
| 4,670,014 A | 6/1987 | Huc et al. |
| 4,709,562 A | 12/1987 | Matsuda |
| 4,748,078 A | 5/1988 | Doi et al. |
| 4,759,354 A | 7/1988 | Quarfoot |
| 4,769,038 A | 9/1988 | Bendavid et al. |
| 4,796,603 A | 1/1989 | Dahlke et al. |
| 4,813,942 A | 3/1989 | Alvarez |
| 4,841,962 A | 6/1989 | Berg et al. |
| 4,854,316 A | 8/1989 | Davis |
| 4,925,294 A | 5/1990 | Geshwind et al. |
| 4,931,546 A | 6/1990 | Tardy et al. |
| 4,942,875 A | 7/1990 | Hlavacek et al. |
| 4,948,540 A | 8/1990 | Nigam |
| 4,950,483 A | 8/1990 | Ksander et al. |
| 4,970,298 A | 11/1990 | Silver et al. |
| 5,002,551 A | 3/1991 | Linsky et al. |
| 5,147,374 A | 9/1992 | Fernandez |
| 5,162,430 A | 11/1992 | Rhee et al. |
| 5,171,273 A | 12/1992 | Silver et al. |
| 5,176,692 A | 1/1993 | Wilk et al. |
| 5,192,301 A | 3/1993 | Kamiya et al. |
| 5,196,185 A | 3/1993 | Silver et al. |
| 5,201,745 A | 4/1993 | Tayot et al. |
| 5,201,764 A | 4/1993 | Kelman et al. |
| 5,206,028 A | 4/1993 | Li |
| 5,217,493 A | 6/1993 | Raad et al. |
| 5,254,133 A | 10/1993 | Seid |
| 5,256,418 A | 10/1993 | Kemp et al. |
| 5,263,983 A | 11/1993 | Yoshizato et al. |
| 5,304,595 A | 4/1994 | Rhee et al. |
| 5,306,500 A | 4/1994 | Rhee et al. |
| 5,324,775 A | 6/1994 | Rhee et al. |
| 5,328,955 A | 7/1994 | Rhee et al. |
| 5,334,527 A | 8/1994 | Brysk |
| 5,339,657 A | 8/1994 | McMurray |
| 5,350,583 A | 9/1994 | Yoshizato et al. |
| 5,356,432 A | 10/1994 | Rutkow et al. |
| 5,368,549 A | 11/1994 | McVicker |
| 5,376,375 A | 12/1994 | Rhee et al. |
| 5,376,376 A | 12/1994 | Li |
| 5,397,331 A | 3/1995 | Himpens et al. |
| 5,399,361 A | 3/1995 | Song et al. |
| 5,413,791 A | 5/1995 | Rhee et al. |
| 5,425,740 A | 6/1995 | Hutchinson, Jr. |
| 5,428,022 A | 6/1995 | Palefsky et al. |
| 5,433,996 A | 7/1995 | Kranzler et al. |
| 5,441,491 A | 8/1995 | Verschoor et al. |
| 5,441,508 A | 8/1995 | Gazielly et al. |
| 5,456,693 A | 10/1995 | Conston et al. |
| 5,456,711 A | 10/1995 | Hudson |
| 5,466,462 A | 11/1995 | Rosenthal et al. |
| 5,480,644 A | 1/1996 | Freed |
| 5,487,895 A | 1/1996 | Dapper et al. |
| 5,490,984 A | 2/1996 | Freed |
| 5,512,291 A | 4/1996 | Li |
| 5,512,301 A | 4/1996 | Song et al. |
| 5,514,181 A | 5/1996 | Light et al. |
| 5,522,840 A | 6/1996 | Krajicek |
| 5,523,348 A | 6/1996 | Rhee et al. |
| 5,536,656 A | 7/1996 | Kemp et al. |
| 5,543,441 A | 8/1996 | Rhee et al. |
| 5,565,210 A | 10/1996 | Rosenthal et al. |
| 5,567,806 A | 10/1996 | Abdul-Malak et al. |
| 5,569,273 A | 10/1996 | Titone et al. |
| RE35,399 E | 12/1996 | Eisenberg |
| 5,593,441 A | 1/1997 | Lichtenstein et al. |
| 5,595,621 A | 1/1997 | Light et al. |
| 5,601,571 A | 2/1997 | Moss |
| 5,607,474 A | 3/1997 | Athanasiou et al. |
| 5,607,590 A | 3/1997 | Shimizu |
| 5,614,587 A | 3/1997 | Rhee et al. |
| 5,618,551 A | 4/1997 | Tardy et al. |
| 5,634,931 A | 6/1997 | Kugel |
| 5,639,796 A | 6/1997 | Lee |
| 5,665,391 A | 9/1997 | Lea |
| 5,667,839 A | 9/1997 | Berg |
| 5,681,568 A | 10/1997 | Goldin et al. |
| 5,686,115 A | 11/1997 | Voumakis et al. |
| 5,690,675 A | 11/1997 | Sawyer et al. |
| 5,695,525 A | 12/1997 | Mulhauser et al. |
| 5,697,978 A | 12/1997 | Sgro |
| 5,700,476 A | 12/1997 | Rosenthal et al. |
| 5,700,477 A | 12/1997 | Rosenthal et al. |
| 5,709,934 A | 1/1998 | Bell et al. |
| 5,716,409 A | 2/1998 | Debbas |
| 5,720,981 A | 2/1998 | Eisinger |
| 5,732,572 A | 3/1998 | Litton |
| 5,749,895 A | 5/1998 | Sawyer et al. |
| 5,752,974 A | 5/1998 | Rhee et al. |
| 5,766,246 A | 6/1998 | Mulhauser et al. |
| 5,766,631 A | 6/1998 | Arnold |
| 5,769,864 A | 6/1998 | Kugel |
| 5,771,716 A | 6/1998 | Schlussel |
| 5,785,983 A | 7/1998 | Furlan et al. |
| 5,800,541 A | 9/1998 | Rhee et al. |
| 5,814,328 A | 9/1998 | Gunasekaran |
| 5,833,705 A | 11/1998 | Ken et al. |
| 5,840,011 A | 11/1998 | Landgrebe et al. |
| 5,861,034 A | 1/1999 | Taira et al. |
| 5,863,984 A | 1/1999 | Doillon et al. |
| 5,869,080 A | 2/1999 | McGregor et al. |
| 5,871,767 A | 2/1999 | Dionne et al. |
| 5,876,444 A | 3/1999 | Lai |
| 5,891,558 A | 4/1999 | Bell et al. |
| 5,899,909 A | 5/1999 | Claren et al. |
| 5,906,937 A | 5/1999 | Sugiyama et al. |
| 5,910,149 A | 6/1999 | Kuzmak |
| 5,911,731 A | 6/1999 | Pham et al. |
| 5,916,225 A | 6/1999 | Kugel |
| 5,919,232 A | 7/1999 | Chaffringeon et al. |
| 5,919,233 A | 7/1999 | Knopf et al. |
| 5,922,026 A | 7/1999 | Chin |
| 5,931,165 A | 8/1999 | Reich et al. |
| 5,942,278 A | 8/1999 | Hagedorn et al. |
| 5,962,136 A | 10/1999 | Dewez et al. |
| 5,972,022 A | 10/1999 | Huxel |
| RE36,370 E | 11/1999 | Li |
| 5,993,844 A | 11/1999 | Abraham et al. |
| 5,994,325 A | 11/1999 | Roufa et al. |
| 5,997,895 A | 12/1999 | Narotam et al. |
| 6,001,895 A | 12/1999 | Harvey et al. |
| 6,008,292 A | 12/1999 | Lee et al. |
| 6,015,844 A | 1/2000 | Harvey et al. |
| 6,039,686 A | 3/2000 | Kovac |
| 6,042,534 A | 3/2000 | Gellman et al. |
| 6,042,592 A | 3/2000 | Schmitt |
| 6,043,089 A | 3/2000 | Sugiyama et al. |

(56) References Cited

U.S. PATENT DOCUMENTS

| | | |
|---|---|---|
| 6,051,425 A | 4/2000 | Morota et al. |
| 6,056,688 A | 5/2000 | Benderev et al. |
| 6,056,970 A | 5/2000 | Greenawalt et al. |
| 6,057,148 A | 5/2000 | Sugiyama et al. |
| 6,063,396 A | 5/2000 | Kelleher |
| 6,066,776 A | 5/2000 | Goodwin et al. |
| 6,066,777 A | 5/2000 | Benchetrit |
| 6,071,292 A | 6/2000 | Makower et al. |
| 6,077,281 A | 6/2000 | Das |
| 6,080,194 A | 6/2000 | Pachence et al. |
| 6,083,522 A | 7/2000 | Chu et al. |
| 6,120,539 A | 9/2000 | Eldridge et al. |
| 6,132,765 A | 10/2000 | DiCosmo et al. |
| 6,143,037 A | 11/2000 | Goldstein et al. |
| 6,153,292 A | 11/2000 | Bell et al. |
| 6,165,488 A | 12/2000 | Tardy et al. |
| 6,171,318 B1 | 1/2001 | Kugel et al. |
| 6,174,320 B1 | 1/2001 | Kugel et al. |
| 6,176,863 B1 | 1/2001 | Kugel et al. |
| 6,179,872 B1 | 1/2001 | Bell et al. |
| 6,197,325 B1 | 3/2001 | MacPhee et al. |
| 6,197,934 B1 | 3/2001 | DeVore et al. |
| 6,197,935 B1 | 3/2001 | Doillon et al. |
| 6,210,439 B1 | 4/2001 | Firmin et al. |
| 6,221,109 B1 | 4/2001 | Geistlich et al. |
| 6,224,616 B1 | 5/2001 | Kugel |
| 6,241,768 B1 | 6/2001 | Agarwal et al. |
| 6,258,124 B1 | 7/2001 | Darois et al. |
| 6,262,332 B1 | 7/2001 | Ketharanathan |
| 6,264,702 B1 | 7/2001 | Ory et al. |
| 6,267,772 B1 | 7/2001 | Mulhauser et al. |
| 6,277,397 B1 | 8/2001 | Shimizu |
| 6,280,453 B1 | 8/2001 | Kugel et al. |
| 6,287,316 B1 | 9/2001 | Agarwal et al. |
| 6,290,708 B1 | 9/2001 | Kugel et al. |
| 6,306,424 B1 | 10/2001 | Vyakarnam et al. |
| 6,312,474 B1 | 11/2001 | Francis et al. |
| 6,328,686 B1 | 12/2001 | Kovac |
| 6,334,872 B1 | 1/2002 | Termin et al. |
| 6,383,201 B1 | 5/2002 | Dong |
| 6,391,333 B1 | 5/2002 | Li et al. |
| 6,391,939 B2 | 5/2002 | Tayot et al. |
| 6,408,656 B1 | 6/2002 | Ory et al. |
| 6,410,044 B1 | 6/2002 | Chudzik et al. |
| 6,413,742 B1 | 7/2002 | Olsen et al. |
| 6,428,978 B1 | 8/2002 | Olsen et al. |
| 6,436,030 B2 | 8/2002 | Rehil |
| 6,440,167 B2 | 8/2002 | Shimizu |
| 6,443,964 B1 | 9/2002 | Ory et al. |
| 6,447,551 B1 | 9/2002 | Goldmann |
| 6,447,802 B2 | 9/2002 | Sessions et al. |
| 6,448,378 B2 | 9/2002 | DeVore et al. |
| 6,451,032 B1 | 9/2002 | Ory et al. |
| 6,451,301 B1 | 9/2002 | Sessions et al. |
| 6,454,787 B1 | 9/2002 | Maddalo et al. |
| 6,477,865 B1 | 11/2002 | Matsumoto |
| 6,479,072 B1 | 11/2002 | Morgan et al. |
| 6,500,464 B2 | 12/2002 | Ceres et al. |
| 6,509,031 B1 | 1/2003 | Miller et al. |
| 6,511,958 B1 | 1/2003 | Atkinson et al. |
| 6,514,286 B1 | 2/2003 | Leatherbury et al. |
| 6,514,514 B1 | 2/2003 | Atkinson et al. |
| 6,540,773 B2 | 4/2003 | Dong |
| 6,541,023 B1 | 4/2003 | Andre et al. |
| 6,548,077 B1 | 4/2003 | Gunasekaran |
| 6,554,855 B1 | 4/2003 | Dong |
| 6,559,119 B1 | 5/2003 | Burgess et al. |
| 6,566,345 B2 | 5/2003 | Miller et al. |
| 6,575,988 B2 | 6/2003 | Rousseau |
| 6,576,019 B1 | 6/2003 | Atala |
| 6,596,002 B2 | 7/2003 | Therin et al. |
| 6,596,304 B1 | 7/2003 | Bayon et al. |
| 6,599,323 B2 | 7/2003 | Melican et al. |
| 6,599,524 B2 | 7/2003 | Li et al. |
| 6,599,690 B1 | 7/2003 | Abraham et al. |
| 6,613,348 B1 | 9/2003 | Jain |
| 6,623,963 B1 | 9/2003 | Muller et al. |
| 6,630,414 B1 | 10/2003 | Matsumoto |
| 6,638,284 B1 | 10/2003 | Rousseau et al. |
| 6,652,594 B2 | 11/2003 | Francis et al. |
| 6,652,595 B1 * | 11/2003 | Nicolo .................. A61F 2/0063 600/36 |
| 6,653,450 B1 | 11/2003 | Berg et al. |
| 6,656,206 B2 | 12/2003 | Corcoran et al. |
| 6,660,280 B1 | 12/2003 | Allard et al. |
| 6,669,735 B1 | 12/2003 | Pelissier |
| 6,682,760 B1 | 1/2004 | Noff et al. |
| 6,685,714 B2 | 2/2004 | Rousseau |
| 6,706,684 B1 | 3/2004 | Bayon et al. |
| 6,706,690 B2 | 3/2004 | Reich et al. |
| 6,719,795 B1 | 4/2004 | Cornwall et al. |
| 6,723,335 B1 | 4/2004 | Moehlenbruck et al. |
| 6,730,299 B1 | 5/2004 | Tayot et al. |
| 6,736,823 B2 | 5/2004 | Darois et al. |
| 6,743,435 B2 | 6/2004 | DeVore et al. |
| 6,755,868 B2 | 6/2004 | Rousseau |
| 6,773,723 B1 | 8/2004 | Spiro et al. |
| 6,783,554 B2 | 8/2004 | Amara et al. |
| 6,790,213 B2 | 9/2004 | Cherok et al. |
| 6,790,454 B1 | 9/2004 | Abdul Malak et al. |
| 6,800,082 B2 | 10/2004 | Rousseau |
| 6,833,408 B2 | 12/2004 | Sehl et al. |
| 6,835,336 B2 | 12/2004 | Wall |
| 6,852,330 B2 | 2/2005 | Bowman et al. |
| 6,869,938 B1 | 3/2005 | Schwartz et al. |
| 6,893,653 B2 | 5/2005 | Abraham et al. |
| 6,896,904 B2 | 5/2005 | Spiro et al. |
| 6,936,276 B2 | 8/2005 | Spiro et al. |
| 6,939,562 B2 | 9/2005 | Spiro et al. |
| 6,949,625 B2 | 9/2005 | Tayot |
| 6,966,918 B1 | 11/2005 | Schuldt-Hempe et al. |
| 6,971,252 B2 | 12/2005 | Therin et al. |
| 6,974,679 B2 | 12/2005 | Andre et al. |
| 6,974,862 B2 | 12/2005 | Ringeisen et al. |
| 6,977,231 B1 | 12/2005 | Matsuda |
| 6,988,386 B1 | 1/2006 | Okawa et al. |
| 7,025,063 B2 | 4/2006 | Snitkin et al. |
| 7,041,868 B2 | 5/2006 | Greene et al. |
| RE39,172 E | 7/2006 | Bayon et al. |
| 7,098,315 B2 | 8/2006 | Schaufler |
| 7,101,381 B2 | 9/2006 | Ford et al. |
| 7,115,220 B2 | 10/2006 | Dubson et al. |
| 7,156,858 B2 | 1/2007 | Schuldt-Hempe et al. |
| 7,175,852 B2 | 2/2007 | Simmoteit et al. |
| 7,192,604 B2 | 3/2007 | Brown et al. |
| 7,207,962 B2 | 4/2007 | Anand et al. |
| 7,214,765 B2 | 5/2007 | Ringeisen et al. |
| 7,226,611 B2 | 6/2007 | Yura et al. |
| 7,229,453 B2 | 6/2007 | Anderson et al. |
| 7,594,921 B2 | 9/2009 | Browning |
| 7,615,065 B2 | 11/2009 | Priewe et al. |
| 7,670,380 B2 | 3/2010 | Cauthen, III |
| 7,709,017 B2 | 5/2010 | Tayot |
| 7,718,556 B2 | 5/2010 | Matsuda et al. |
| 7,732,354 B2 | 6/2010 | Fricke et al. |
| 7,785,334 B2 | 8/2010 | Ford et al. |
| 7,799,767 B2 | 9/2010 | Lamberti et al. |
| 7,806,905 B2 | 10/2010 | Ford et al. |
| 7,824,420 B2 | 11/2010 | Eldridge et al. |
| 8,142,515 B2 | 3/2012 | Therin et al. |
| 8,197,837 B2 | 6/2012 | Jamiolkowski et al. |
| 8,323,675 B2 | 12/2012 | Greenawalt |
| 8,366,787 B2 | 2/2013 | Brown et al. |
| 8,709,094 B2 | 4/2014 | Stad et al. |
| 8,846,060 B2 | 9/2014 | Archibald et al. |
| 8,877,233 B2 | 11/2014 | Obermiller et al. |
| 8,956,373 B2 | 2/2015 | Ford et al. |
| 9,034,357 B2 | 5/2015 | Stopek |
| 2002/0095218 A1 | 7/2002 | Carr et al. |
| 2003/0086975 A1 | 5/2003 | Ringeisen |
| 2003/0114937 A1 | 6/2003 | Leatherbury et al. |
| 2003/0130745 A1 | 7/2003 | Cherok et al. |
| 2003/0133967 A1 | 7/2003 | Ruszczak et al. |
| 2003/0225355 A1 | 12/2003 | Butler |

(56) References Cited

U.S. PATENT DOCUMENTS

| | | | |
|---|---|---|---|
| 2004/0034373 A1 | 2/2004 | Schuldt-Hempe et al. | |
| 2004/0059356 A1 | 3/2004 | Gingras | |
| 2004/0101546 A1 | 5/2004 | Gorman et al. | |
| 2005/0002893 A1 | 1/2005 | Goldmann | |
| 2005/0021058 A1 | 1/2005 | Negro | |
| 2005/0085924 A1 | 4/2005 | Darois et al. | |
| 2005/0113849 A1 | 5/2005 | Popadiuk et al. | |
| 2005/0137512 A1 | 6/2005 | Campbell et al. | |
| 2005/0142161 A1 | 6/2005 | Freeman et al. | |
| 2005/0148963 A1 | 7/2005 | Brennan | |
| 2005/0175659 A1 | 8/2005 | Macomber et al. | |
| 2005/0232979 A1 | 10/2005 | Shoshan | |
| 2005/0267521 A1 | 12/2005 | Forsberg | |
| 2005/0288691 A1 | 12/2005 | Leiboff | |
| 2006/0064175 A1 | 3/2006 | Pellssier et al. | |
| 2006/0135921 A1 | 6/2006 | Wiercinski et al. | |
| 2006/0147501 A1 | 7/2006 | Hillas et al. | |
| 2006/0216320 A1 | 9/2006 | Kitazono et al. | |
| 2006/0252981 A1 | 11/2006 | Matsuda et al. | |
| 2007/0265710 A1* | 11/2007 | Brown .................. | A61F 2/0063 623/23.72 |
| 2007/0299538 A1 | 12/2007 | Roeber | |
| 2010/0189764 A1* | 7/2010 | Thomas ................ | A61F 2/0063 424/426 |
| 2012/0010636 A1* | 1/2012 | Boey .................... | A61F 2/0063 606/151 |

FOREIGN PATENT DOCUMENTS

| | | |
|---|---|---|
| DE | 10019604 A1 | 10/2001 |
| DE | 10043396 C1 | 6/2002 |
| EP | 0194192 A1 | 9/1986 |
| EP | 0248544 A1 | 12/1987 |
| EP | 0276890 A2 | 8/1988 |
| EP | 0372969 A1 | 6/1990 |
| EP | 544485 A1 | 6/1993 |
| EP | 0552576 A1 | 7/1993 |
| EP | 614650 A2 | 9/1994 |
| EP | 0621014 A1 | 10/1994 |
| EP | 0625891 A1 | 11/1994 |
| EP | 0637452 A1 | 2/1995 |
| EP | 0705878 A2 | 4/1996 |
| EP | 0719527 A1 | 7/1996 |
| EP | 0774240 A1 | 5/1997 |
| EP | 0797962 A2 | 10/1997 |
| EP | 827724 A2 | 3/1998 |
| EP | 0836838 A1 | 4/1998 |
| EP | 0895762 A2 | 2/1999 |
| EP | 898944 A2 | 3/1999 |
| EP | 1017415 A1 | 7/2000 |
| EP | 1052319 A1 | 11/2000 |
| EP | 1055757 A1 | 11/2000 |
| EP | 1 216 717 A1 | 6/2002 |
| EP | 1 216 718 A1 | 6/2002 |
| EP | 0693523 B1 | 11/2002 |
| EP | 1315468 A2 | 6/2003 |
| EP | 1382728 A1 | 1/2004 |
| EP | 1484070 A1 | 12/2004 |
| EP | 1561480 A2 | 8/2005 |
| EP | 1782848 A2 | 5/2007 |
| FR | 2244853 A1 | 4/1975 |
| FR | 2257262 A1 | 8/1975 |
| FR | 2 308 349 A1 | 11/1976 |
| FR | 2453231 A1 | 10/1980 |
| FR | 2715405 A1 | 7/1995 |
| FR | 2 724 563 A1 | 3/1996 |
| FR | 2744906 A1 | 8/1997 |
| FR | 2766698 A1 | 2/1999 |
| FR | 2771622 A1 | 6/1999 |
| FR | 2779937 A1 | 12/1999 |
| FR | 2859624 A1 | 3/2005 |
| FR | 2863277 A1 | 6/2005 |
| FR | 2884706 A1 | 10/2006 |
| GB | 2 051 153 A | 1/1981 |
| JP | H0332677 A | 2/1991 |
| JP | H05237128 A | 9/1993 |
| JP | H09137380 A | 5/1997 |
| WO | 89/02445 A1 | 3/1989 |
| WO | 89/08467 A1 | 9/1989 |
| WO | 90/12551 A1 | 11/1990 |
| WO | 92/06639 A2 | 4/1992 |
| WO | 92/20349 A1 | 11/1992 |
| WO | 93/11805 A1 | 6/1993 |
| WO | 93/18174 A1 | 9/1993 |
| WO | 94/17747 A1 | 8/1994 |
| WO | 95/07666 A1 | 3/1995 |
| WO | 95/18638 A1 | 7/1995 |
| WO | 95/32687 A1 | 12/1995 |
| WO | 96/03091 A1 | 2/1996 |
| WO | 96/08277 A1 | 3/1996 |
| WO | 96/09795 A1 | 4/1996 |
| WO | 96/14805 A1 | 5/1996 |
| WO | 96/41588 A1 | 12/1996 |
| WO | 97/35533 A1 | 10/1997 |
| WO | 98/35632 A1 | 8/1998 |
| WO | 98/49967 A1 | 11/1998 |
| WO | 99/05990 A1 | 2/1999 |
| WO | 99/06079 A1 | 2/1999 |
| WO | 99/06080 A1 | 2/1999 |
| WO | 99/51163 A1 | 10/1999 |
| WO | 00/16821 A1 | 3/2000 |
| WO | 00/67663 A1 | 11/2000 |
| WO | 01/15625 A1 | 3/2001 |
| WO | 01/80773 A1 | 11/2001 |
| WO | 02/007648 A1 | 1/2002 |
| WO | WO 02/22047 A1 | 3/2002 |
| WO | 02/078568 A1 | 10/2002 |
| WO | 03/002168 A1 | 1/2003 |
| WO | 2004004600 A1 | 1/2004 |
| WO | 2004071349 A2 | 8/2004 |
| WO | 2004078120 A2 | 9/2004 |
| WO | 2004103212 A1 | 12/2004 |
| WO | 200511280 A1 | 2/2005 |
| WO | 2005013863 A2 | 2/2005 |
| WO | 2005018698 A1 | 3/2005 |
| WO | 2005105172 A1 | 11/2005 |
| WO | 2006018552 A1 | 2/2006 |
| WO | 2006023444 A2 | 3/2006 |
| WO | 2007048099 A2 | 4/2007 |
| WO | 2009031035 A2 | 3/2009 |
| WO | 2009071998 A2 | 6/2009 |
| WO | 2009126476 A1 | 10/2009 |
| WO | WO 2011042553 A1 * | 4/2011 ........... A61F 2/0063 |
| WO | WO 2013/007534 A1 | 1/2013 |
| WO | WO 2013/017836 A2 | 2/2013 |

OTHER PUBLICATIONS

Malette, W. G. et al., "Chitosan, A New Hemostatic," Ann Th. Surg., Jul. 1983, pp. 55-58, 36.

Langenbech, M. R. et al., "Comparison of biomaterials in the early postoperative period," Surg Endosc., May 2003, pp. 1105-9, 17 (7).

Bracco, P. et al., "Comparison of polypropylene and polyethylene terephthalate (Dacron) meshes for abdominal wall hernia repair: A chemical and morphological study," Hernia, 2005, pp. 51-55, 9 (1), published online Sep. 2004.

Klinge, U. et al., "Foreign Body Reaction to Meshes Used for the Repair of Abdominal Wall Hernias," Eur J. Surg, Sep. 1999, pp. 665-673, 165.

Logeart, D. et al., "Fucans, sulfated polysaccharides extracted from brown seaweeds, inhibit vascular smooth muscle cell proliferation. II. Degradation and molecular weight effect," Eur. J. Cell. Biol., Dec. 1997, pp. 385-390, 74(4).

Haneji, K. et al., "Fucoidan extracted from Cladosiphon Okamuranus Tokida Induces Apoptosis of Human T-Cell Leukemia Virus Type 1-Infected T-Cell Lines and Primary Adult T-Cell Leukemia Cells," Nutrition and Cancer, 2005, pp. 189-201, 52(2), published online Nov. 2009.

Junge, K. et al., "Functional and Morphologic Properties of a Modified Mesh for Inguinal Hernia Repair," World J. Surg., Sep. 2002, pp. 1472-1480, 26.

(56) References Cited

OTHER PUBLICATIONS

Klinge, U. et al., "Functional and Morphological Evaluation of a Low-Weight, Monofilament Polypropylene Mesh for Hernia Repair," J. Biomed. Mater. Res., Jan. 2002, pp. 129-136, 63.

Welty, G. et al., "Functional impairment and complaints following incisional hernia repair with different polypropylene meshes," Hernia, Aug. 2001; pp. 142-147, 5.

Varum, K. et al., "In vitro degradation rates of partially N-acetylated chitosans in human serum," Carbohydrate Research, Mar. 1997, pp. 99-101, 299.

Haroun-Bouhedja, F. et al., "In Vitro Effects of Fucans on MDA-MB231 Tumor Cell Adhesion and Invasion," Anticancer Res., Jul.-Aug. 2002, pp. 2285-2292, 22(4).

Scheidbach, H. et al., "In vivo studies comparing the biocompatibility of various polypropylene meshes and their handling properties during endoscopic total extraperitoneal (TEP) patchplasty: An experimental study in pigs," Surg. Endosc., Feb. 2004, pp. 211-220, 18(2).

Blondin, C. et al., "Inhibition of Complement Activation by Natural Sulfated Polysaccharides (Fucans) from Brown Seaweed," Molecular Immuol., Mar. 1994, pp. 247-253, 31(4).

Zvyagintseva, T. et al., "Inhibition of complement activation by water-soluble polysaccharides of some far-eastern brown seaweeds," Comparative Biochem and Physiol, Jul. 2000, pp. 209-215, 126(3).

Rosen, M. et al., "Laparoscopic component separation in the single-stage treatment of infected abdominal wall prosthetic removal," Hernia, 2007, pp. 435-440, 11, published online Jul. 2007.

Amid, P., "Lichtenstein tension-free hernioplasty: Its inception, evolution, and principles," Hernia, 2004; pp. 1-7, 8, published online Sep. 2003.

Boisson-Vidal, C. et al., "Neoangiogenesis Induced by Progenitor Endothelial Cells: Effect of Fucoidan From Marine Algae," Cardiovascular & Hematological Agents in Medicinal Chem., Jan. 2007, pp. 67-77, 5(1).

O'Dwyer, P. et al., "Randomized clinical trial assessing impact of a lightweight or heavyweight mesh on chronic pain after inguinal hernia repair," Br. J. Surg., Feb. 2005, pp. 166-170, 92(2).

Muzzarelli, R. et al., "Reconstruction of parodontal tissue with chitosan," Biomaterials, Nov. 1989, pp. 598-604, 10.

Haroun-Bouhedja, F. et al., "Relationship between sulfate groups and biological activities of fucans," Thrombosis Res., Dec. 2000, pp. 453-459, 100(5).

Blondin, C. et al., "Relationships between chemical characteristics and anticomplementary activity of fucans," Biomaterials, Mar. 1996, pp. 597-603, 17(6).

Strand, S. et al., "Screening of Chitosans and Conditions for Bacterial Flocculation," Biomacromolecules, Mar. 2001, 126-133, 2.

Kanabar, V. et al., "Some structural determinants of the antiproliferative effect of heparin-like molecules on human airway smooth muscle," Br. J. Pharmacol., Oct. 2005, pp. 370-777, 146(3).

Hirano, S. et al., "The blood biocompatibility of chitosan and N-acylchitosans," J. Biomed. Mater. Res., Apr. 1985, 413-417, 19.

Rao, B. et al., "Use of chitosan as a biomaterial: Studies on its safety and hemostatic potential," J. Biomed. Mater. Res., Jan. 1997, pp. 21-28, 34.

Prokop, A. et al., "Water Soluble Polymers for Immunoisolation I: Complex Coacevation and Cytotoxicity," Advances in Polymer Science, Jul. 1998, pp. 1-51, 136.

Collins, R. et al., "Use of collagen film as a dural substitute: Preliminary animal studies," Journal of Biomedical Materials Research, Feb. 1991, pp. 267-276, vol. 25.

Preliminary Search Report from French Patent Office dated Dec. 20, 2006, 3 pages.

International Search Report for PCT/EP14/061654 date of completion is Jul. 9, 2014 (3 pages).

Examination Report for Australian Application No. 2014276850 dated Mar. 9, 2018, 3 pages.

Communication pursuant to Article 94(3) EPC issued in European Patent Application No. 14729283.3 dated Feb. 15, 2019, 4 pages.

Australian Examination Report for application No. 2014278850 dated Jul. 27, 2018 (5 pages).

\* cited by examiner

TEXTILE-BASED PROTHESIS FOR LAPAROSCOPIC SURGERY

CROSS-REFERENCE TO RELATED APPLICATIONS

This application is a National Stage Application of PCT/EP14/061654 under 35 USC § 371 (a), which claims priority of French Patent Application Serial No. 13/55258 filed Jun. 7, 2013, the disclosures of each of the above-identified applications are hereby incorporated by reference in their entirety.

The present invention relates to a prosthesis based on a biocompatible textile and more particularly intended to be implanted by laparoscopy, such as, for example, the wall reinforcement prostheses for repair of hernias.

Wall reinforcement prostheses, for example for the abdominal wall, are widely used in surgery. These prostheses are intended to treat hernias by temporarily or permanently filling a tissue defect. These prostheses are generally made from a biocompatible prosthetic textile and can have a number of shapes, for example rectangular, circular or oval, depending on the anatomical structure to which they are to adapt. Some of these prostheses are made from entirely bioresorbable filaments and are intended to disappear after they have performed their reinforcing function during the period of cellular colonization and tissue rehabilitation. Others comprise non-bioresorbable filaments and are intended to remain permanently in the body of the patient.

Moreover, in order to minimize the trauma subsequent to any surgical intervention, patients are increasingly operated on by laparoscopy when the type of intervention performed allows this. Laparoscopy requires only very small incisions through which a trocar is passed, with the prosthesis being conveyed inside the trocar to the implantation site. Open surgery is thus avoided, and the patient can soon leave hospital. Laparoscopy is particularly popular in surgical interventions performed in the abdomen, for example the treatment of hernias.

However, the trocars used in laparoscopic surgery generally have a relatively small calibrated diameter, which may vary, for example, from 5 to 15 mm, in order to reduce as much as possible the size of the incision that is made. The prosthesis therefore has to be conveyed within a conduit of small diameter and must then be deployed at the implantation site.

To carry out this step, the prosthesis is generally rolled up on itself in order to make it slide in the conduit of the trocar or is introduced directly by force. For this step, the surgeon generally uses laparoscopy forceps to push/guide the prosthesis inside the trocar. These forceps take up a lot of space in the trocar. The small diameter of the trocar makes this step particularly difficult to carry out. If the rolling-up of the prosthesis is not correctly guided and effected, the textile may form a plug in the trocar. The prosthesis no longer slides inside the trocar, and it is very complicated to remove it from the latter. Moreover, even when the prosthesis has been correctly rolled up, the emergence of the prosthesis from the trocar and the deployment of the prosthesis at the implantation site are complex steps. Indeed, the surgeon initially has to pull on the prosthesis in order to free it from the trocar, but without damaging it. He then has to deploy the prosthesis and spread the latter out perfectly. If the prosthesis does not spread out perfectly against the abdominal wall for example, there may be a risk of a soft organ being inserted between the prosthesis and said wall, which can lead to risks of adherence, pain and intestinal occlusion and can increase the possibility of recurrence. It is therefore essential for the surgeon to ensure that no part of the prosthesis is folded and that no viscera or part of the intestine is caught between the prosthesis and the abdominal wall. However, on account of the limited space at the implantation site, it may prove complicated to deploy the prosthesis and then to orient it suitably with respect to the surrounding anatomical structures.

There is therefore still the need for a prosthesis that is based on a biocompatible textile, that can be used for the repair of hernias, that can be easily introduced into a conduit such as that of a trocar of small diameter, without damaging said textile, and that is able to be deployed completely, and preferably easily, once the implantation site in the body of the patient has been reached.

The present invention aims to meet such a need.

A first aspect of the invention concerns a prosthesis comprising:

at least one flexible biocompatible textile of generally elongate shape defining a longitudinal axis, said textile being delimited by a peripheral outer edge forming substantially two opposite long sides and two opposite short sides, and at least one reinforcing element for said textile, characterized in that said reinforcing element is in the form of a resilient frame connected to said textile along substantially the peripheral edge of the textile, said frame forming, in the area of each short side of the textile, at least one U-shaped bend extending in the direction of the longitudinal axis, said frame being able to adopt an unstressed configuration, in which said textile is deployed, and a stressed configuration, in which said frame is subjected to a radial force directed towards said longitudinal axis and said textile forms at least one longitudinal fold.

The prosthesis according to the invention is able to be folded up along at least one longitudinal fold in a very simple way, for example by pressing the frame together, in one hand, radially in the direction of the longitudinal axis of the prosthesis. Thus, the prosthesis is capable of adopting an elongate configuration, which is very compact in the radial direction, allowing it to pass easily through a trocar, without the aid of additional tools. The frame is sufficiently resilient to allow the prosthesis to be folded in order to enter a trocar of small diameter, for example a diameter of 5 to 15 mm. When it emerges from the trocar, the prosthesis is then capable of deploying automatically under the action of the frame, which recovers its initial configuration in the absence of the stresses from the walls of the trocar. The prosthesis is capable of conforming to the anatomical structures and of remaining in place once it has emerged from the trocar.

According to the present invention, "textile" is understood as any arrangement or assembly of biocompatible yarns, fibres, filaments and/or multifilaments, for example obtained by knitting, weaving, braiding, or nonwoven.

In the present application, "biocompatible" is understood as meaning that the materials having this property can be implanted in the human or animal body.

Within the meaning of the present application, a "flexible textile" is understood as a textile that can be folded up but that does not have an inherent elasticity allowing it to spontaneously recover a spread-out configuration once it has been folded up.

Within the meaning of the present application, a "resilient frame" is understood as a frame which, for example, can be semi-rigid and has a resiliency or elasticity allowing it to be deformed under the effect of a temporary stress and allowing it to return to an initial state of rest once said stress has been removed. According to the present invention, the frame allows the textile, and therefore the prosthesis, to be pressed together in the radial direction towards the longitudinal axis of the textile.

This step of pressing together is made easier by the presence of the U-shaped bends, which are disposed on the short sides of the frame and give the frame an additional elasticity. Thus, under the effect of the radial stress exerted on the long sides of the frame, the U-shaped bends form a hard point acting as a guide element aligned on the longitudinal axis of the prosthesis, making it easier to introduce the prosthesis into a trocar in the direction of the longitudinal axis of the prosthesis and of the trocar.

The materials that may be suitable for producing the frame of the prosthesis according to the invention may be chosen from any biocompatible material having a certain rigidity in order to meet the requirements described above.

In one embodiment, the frame is made of a bioresorbable material. In the present application, "bioresorbable" or "biodegradable" is understood to mean that the materials having this property are absorbed and/or degraded by the tissues or washed from the implantation site and disappear in vivo after a certain time, which may vary, for example, from a few hours to a few months, depending on the chemical nature of the materials.

Thus, the frame acts as a guide for the prosthesis for introducing the latter into a trocar, then acts as a means of stiffening the prosthesis during the positioning and implanting of the prosthesis, after which it gradually degrades when the textile has been recolonized by the surrounding cells.

For example, the bioresorbable material can be chosen from among polylactic acid (PLA), polycaprolactones (PCL), polydioxanones (PDO), trimethylene carbonates (TMC), polyvinyl alcohol (PVA), polyhydroxyalkanoates (PHA), oxidized cellulose, polyglycolic acid (PGA), copolymers of these materials and mixtures thereof. For example, the bioresorbable material can be a copolymer of polylactic acid and of polyglycolic acid.

Alternatively, the frame of the prosthesis according to the invention is made of a non-bioresorbable material chosen from among polypropylenes, polyesters such as polyethyleneterephthalates, polyamides, silicones, polyether ether ketone (PEEK), polyarylether ether ketone (PAEK), polyurethanes and mixtures thereof.

In another embodiment, said frame is formed by a combination of bioresorbable material and of non-bioresorbable material.

The frame of the prosthesis according to the invention substantially follows the peripheral edge of the textile, in other words it is substantially parallel to this edge, and can, for example, be set back from the peripheral outer edge of the textile. Thus, by adopting the shape of the contour of the textile, the frame can have an outer perimeter lower than that of the peripheral outer edge of the textile. In other words, the peripheral outer edge of the textile can extend beyond the frame by a certain distance. For example, this distance can be greater than or equal to 1 mm. In other words, the frame and the peripheral outer edge of the textile are of similar geometrical shape, but the frame can have smaller dimensions than those of the peripheral outer edge of the textile.

In one embodiment, for each short side, said U-shaped bend extends towards the outside of said frame. Thus, during the step of pressing together, each U-shaped bend forms a loop and therefore a hard point facilitating the introduction of the pressed-together prosthesis into a trocar of small diameter, for example a diameter of 5-15 mm. Then, when the prosthesis emerges from the trocar, the absence of stress exerted on the long sides of the frame allows the latter to redeploy naturally and automatically, and the textile recovers its initial spread-out configuration.

In one embodiment, for each short side, said U-shaped bend extends towards the inside of said frame. For example, the frame can form a supplementary bend in the area of each long side, said supplementary bend extending towards the inside of the frame in a direction perpendicular to the longitudinal axis A. Such a shape of the frame makes it possible to easily press the prosthesis together and align it on the longitudinal axis A. Since the U-shaped bend of each short side extends towards the inside of the frame, the step of pressing together causes the formation of two stubs at the ends of the pressed-together prosthesis, these two stubs making it easier to introduce the prosthesis into the trocar.

In one embodiment, said frame is continuous. Thus, the step of pressing the prosthesis together, by pressing the frame together towards the longitudinal axis of the prosthesis, does not create any projecting elements that could potentially perforate and damage the tissues. By virtue of its nature and its shape, the frame only has rounded and atraumatic outer contours.

The frame of the prosthesis according to the invention is connected to said textile. For example, the frame can be fixed to the textile by sewing, ultrasonic welding, or else by adhesive bonding or moulding.

In one embodiment, the frame of the prosthesis according to the invention is moulded over the textile. Thus, the frame is connected to the textile by injection moulding of one or more thermoplastic or thermosetting biocompatible materials. For example, the mould of an injection-moulding machine is equipped with an insert gate in which the textile is held. One or more thermoplastic or thermosetting biocompatible materials are then heated to their melting point and injected into the mould, the latter having one or more channels of the shape desired for the frame. The holding of the textile, the precision of the injection volume and the choice of the injection parameters make it possible to obtain a frame without material loss, without flash and with good surface evenness. Such a method allows the frame to be fixed to the textile in a particularly effective and lasting way.

In one embodiment, the frame is obtained by moulding a copolymer of polylactic acid and of polyglycolic acid over the textile.

The textile of the prosthesis according to the invention has a generally elongate shape, for example rectangular, oval or elliptic. The textile can have another initial shape and can then be cut to such an elongate shape, in particular to a shape adapted to the defect, for example the hernia defect, that is to be treated.

In one embodiment, said generally elongate shape is a rectangle. In another embodiment, said generally elongate shape is an ellipse. Such a shape is particularly advantageous, since it is similar to the anatomical shape of the defect that is to be filled. Moreover, when pressed together, such a prosthesis adopts a shape that is perfectly aligned on its longitudinal axis, permitting easier introduction into a trocar, even one of small diameter.

In one embodiment, the textile is a mesh.

Within the meaning of the present application, a "mesh" is understood as a textile, as defined above, which is openworked, that is to say provided with pores that favour recolonization of tissue. Such a mesh can be bioresorbable, permanent or partially bioresorbable. It is sufficiently flexible to be folded up at the time of introduction into the abdominal cavity. The mesh can be made from a layer of textile or several layers of textile. Such meshes are well known to a person skilled in the art.

In one embodiment of the invention, the mesh is a knit. By virtue of the meshwork of the knit, it is possible to obtain openworked faces that promote cell recolonization after implantation. The knit can be two-dimensional or three-dimensional.

Within the meaning of the present application, a two-dimensional knit is understood as a knit having two opposite faces linked to each other by meshes but devoid of a spacer giving it a certain thickness: such a knit can be obtained, for example, by knitting yarns on a warp knitting machine or raschel knitting machine using two guide bars. Examples of knitting two-dimensional knits suitable for the present invention are given in the document WO2009/071998.

According to the present application, a three-dimensional knit is understood as a knit having two opposite faces linked to each other by a spacer that gives the knit a significant thickness, said spacer itself being formed from additional linking yarns in addition to the yarns forming the two faces of the knit. Such a knit can be obtained, for example, on a double-bed warp knitting or raschel knitting machine using several guide bars. Examples of knitting three-dimensional knits suitable for the present invention are given in the documents WO99/05990, WO2009/031035 and WO2009/071998.

In one embodiment of the invention, one face of the textile is covered by a non-stick coating.

Such a non-stick coating makes it possible in particular to avoid the formation of undesired and serious post-surgical fibrous adhesions.

Within the meaning of the present application, "non-stick" is understood as a smooth and non-porous biocompatible material or coating that does not offer space for cell recolonization and that preferably promotes the growth of peritoneum.

Another aspect of the present invention is a method by which a prosthesis of the kind described above is conveyed to an implantation site, said method comprising the following steps:
the above prosthesis is pressed together in one hand, by folding the two long sides of the textile over towards the medial longitudinal axis of the prosthesis,
the longitudinal axis of the prosthesis, which has thereby been made compact, is lined up with the longitudinal axis of a trocar intended to receive said prosthesis,
said bend is introduced into the proximal orifice of the trocar, and the compact prosthesis is pushed through the inside of the trocar by a force directed along the longitudinal axis of the trocar.

The prosthesis is thus pushed along the longitudinal axis of the trocar until its end emerges from the trocar via the distal orifice thereof.

The push is continued until the prosthesis has deployed completely outside the trocar. It may be possible to use forceps to pull on the distal end of the prosthesis, or to use a pusher to continue pushing the prosthesis in the trocar.

In this application, the distal end of a device means the end farthest from the hand of the user, and the proximal end means the end nearest to the hand of the user. Likewise in this application, the term "distal direction" means the direction of introduction of the prosthesis into the body of the patient, and the term "proximal direction" means the direction opposite to this direction of introduction.

By virtue of the structure of the prosthesis according to the invention, the step of introducing the bend into the trocar is greatly facilitated. Likewise, with the prosthesis made perfectly compact, it passes through the trocar easily and without damage.

Finally, the automatic return of the frame to its initial configuration brings about the automatic deployment of the prosthesis and the perfect spreading-out of the latter at the implantation site.

Figure 2:
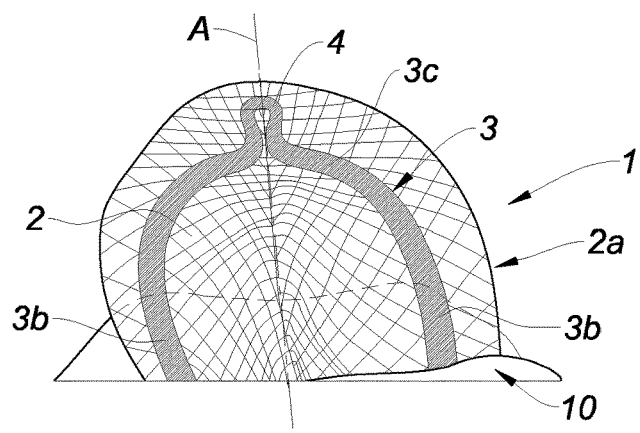
Figure 3:
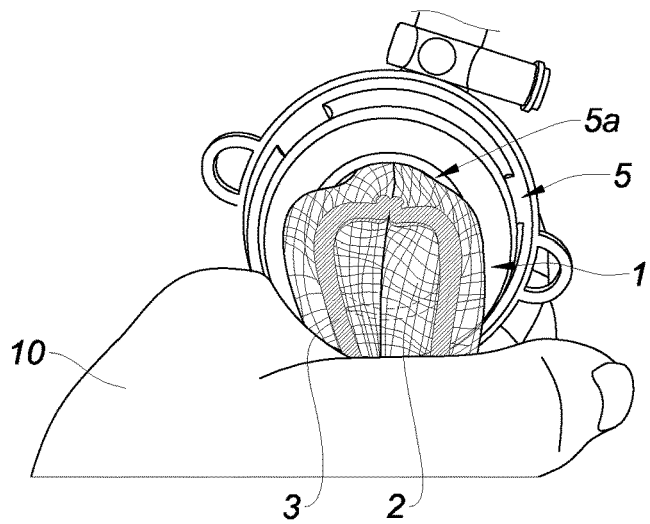
Figure 4:
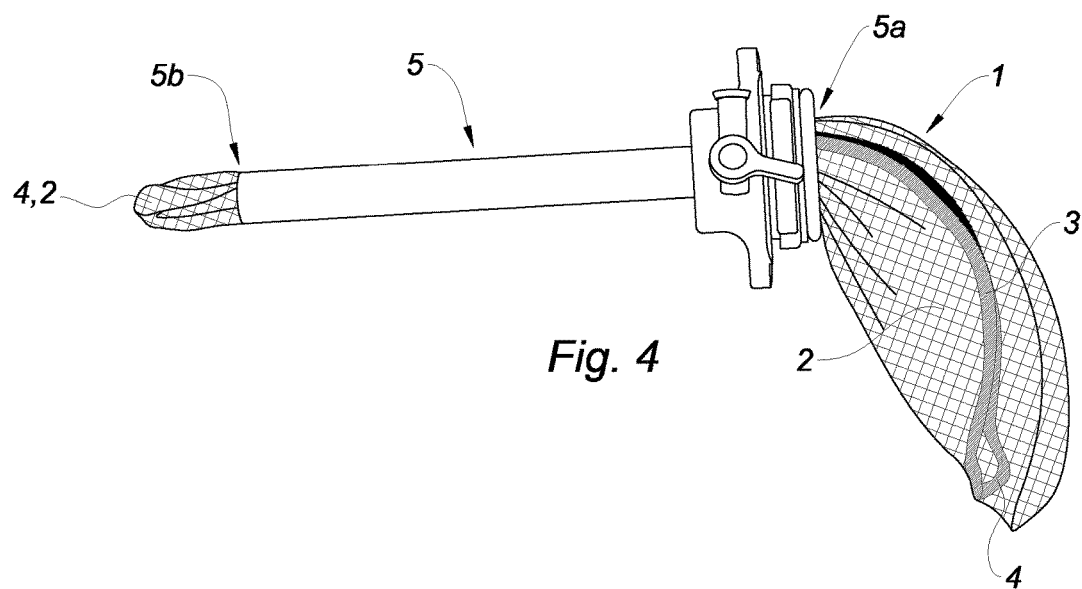
Figure 5:
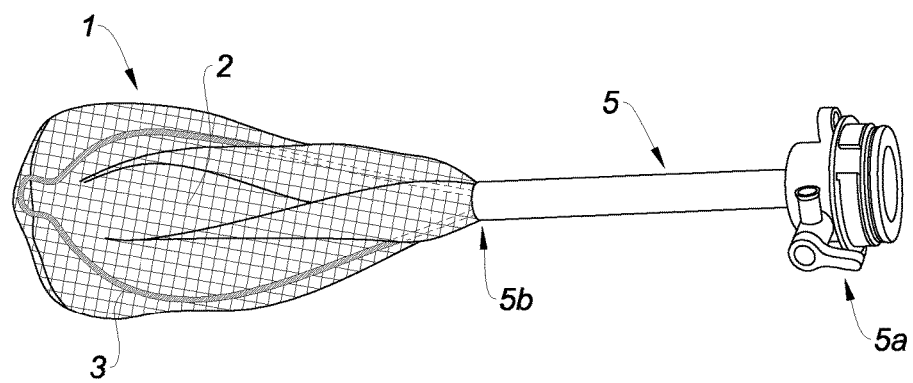
Figure 6:
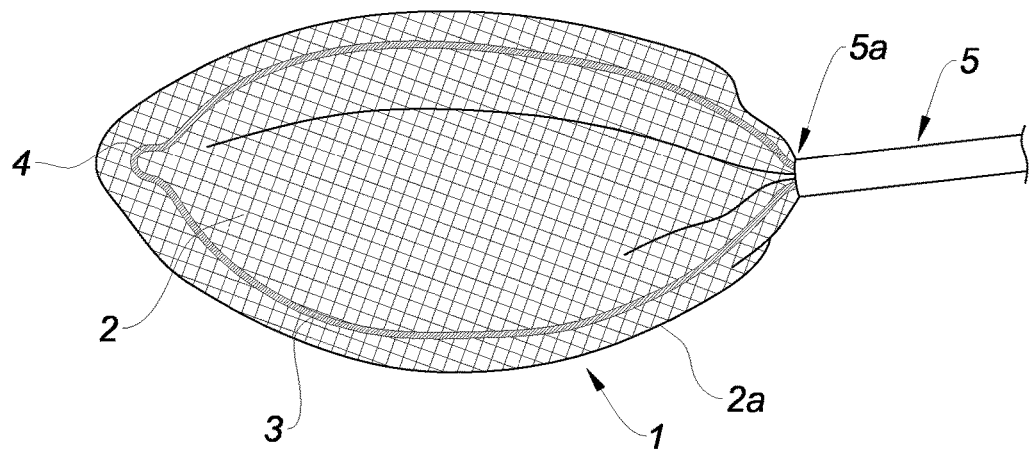
Figure 7:
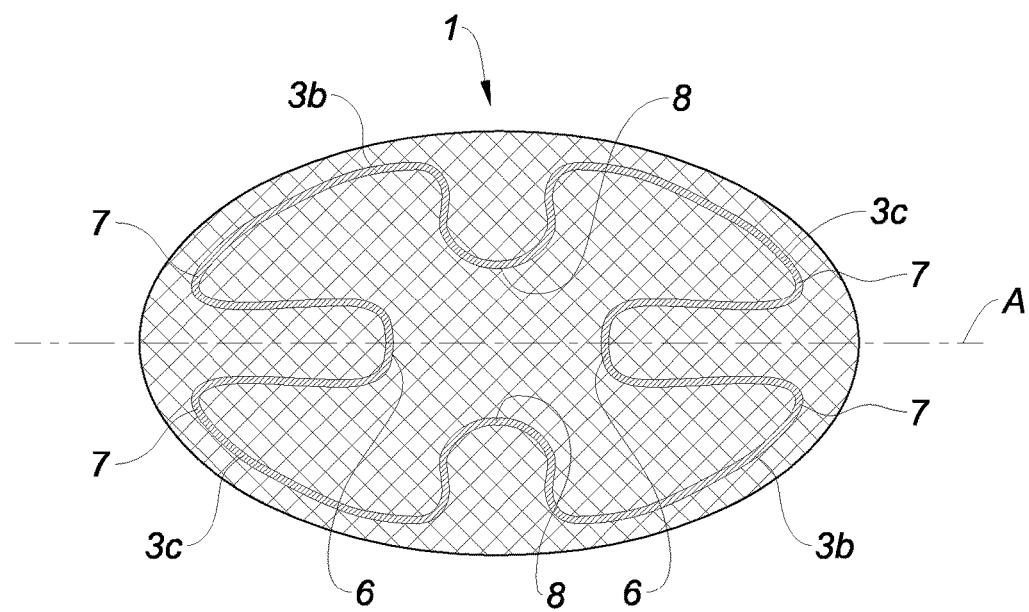

The advantages of the present invention will become clearer from the following detailed description and from the attached drawings in which:

FIG. 1 shows a plan view of a first embodiment of a prosthesis according to the invention, FIG. 2 shows a perspective view of one end of the prosthesis from FIG. 1, when the prosthesis is in the compact shape, FIG. 3 shows the step of introducing one end of the prosthesis from FIG. 2 into the proximal orifice of a trocar, FIG. 4 is a side view of the prosthesis from FIG. 1 in the compact shape and partially introduced into the trocar from FIG. 3, FIG. 5 is a side view of the prosthesis from FIG. 1 in the compact shape and partially emerging from the trocar of FIG. 3, FIG. 6 is a side view showing the automatic deployment of the prosthesis from FIG. 1 when it has emerged almost completely from the trocar of FIG. 3, FIG. 7 is a plan view of a second embodiment of the prosthesis according to the invention.

FIG. 1 shows an embodiment of a prosthesis 1 according to the invention. The prosthesis 1 comprises a biocompatible textile 2 and a reinforcing element in the form of a frame 3.

As will be clear from FIG. 1, the textile 2 has a generally elongate shape defining a longitudinal axis A. The textile 2 is thus delimited by a peripheral outer edge 2a forming substantially two opposite long sides 2b, which are substantially parallel to the longitudinal axis A, and two opposite short sides 2c, which are substantially perpendicular to the longitudinal axis A. In the example shown, the textile 2 has the general shape of an ellipse. Such a shape is suitable for the repair of a hernia of the abdominal wall, for example.

In other embodiments, the textile 2 could have an oval shape or a rectangular shape or could be protean if the shape in question is generally elongate and defines a longitudinal axis.

The textile 2 is made up of an arrangement of biocompatible filaments, such as a knit, a woven or a nonwoven. Preferably, as is shown in FIG. 1, the textile 2 is in the form of a mesh, that is to say it has openings for better tissue integration. For example, the textile 1 can be a two-dimensional or three-dimensional knit. Such textiles in the form of meshes or knits are well known to a person skilled in the art and are not described in any greater detail here.

The textile 2 can be bioresorbable, permanent or partially bioresorbable. As will become clear from the description below, the textile 2 is sufficiently flexible to be folded up, in particular at the time of introduction of the prosthesis into a trocar, along one or more longitudinal folds. In general, however, the textile 2 does not have an inherent elasticity allowing it to spontaneously recover a spread-out configuration once it has been folded up. The textile 2 can be supplied in the form of a band, which one cuts to the dimensions of the defect to be treated.

Referring again to FIG. 1, and as will become clear on reading the description below, the frame 3 acts as an element reinforcing the textile 2 in order to stiffen the latter and keep it in its generally elongate shape, as a tool for guiding the prosthesis 1 at the time of its introduction into a trocar, and as a tool for assisting in the deployment of the prosthesis when the latter emerges from the trocar at the implantation site. For this purpose, the frame 3 is connected to the textile 2 and has an elasticity allowing it to be deformed under the effect of a temporary stress and allowing it to return to an initial state of rest once said stress has been removed.

The frame 3 is connected to the textile 2. It can be attached to the textile 2 by means of a seam, or else by means of an ultrasonic weld, by adhesive bonding, or by injection moulding.

In one embodiment, the frame 3 is connected to the textile 2 by injection moulding of one or more thermoplastic or thermosetting biocompatible materials. Such an embodiment makes it possible to secure the fixing of the frame to the textile in a particularly effective manner and to produce the prostheses according to the invention at an industrial scale.

In the injection moulding technique, a mould is formed in which, for example, there is a cavity defining a contour which corresponds to the contour of the frame that is to be obtained, namely a generally elliptical contour as regards the example shown in FIGS. 1 and 2. The textile is held in an insert gate of the mould. The thermoplastic material used to produce the frame, for example a copolymer of polylactic acid and of polyglycolic acid, is heated and injected into the cavity using an injection moulding machine.

After the injection step, the mould is opened and the prosthesis 1 is withdrawn from the mould. Such a method allows the textile to be "embedded" in the part moulded over it. Thus, the frame 3, which is the overmoulded part, is connected to the textile, without any risk of its coming loose or fragmenting.

The frame 3 is continuous. Thus, as will become clear from the description below, the step of pressing the prosthesis together, by pressing the frame together towards the longitudinal axis of the prosthesis, does not create any projecting elements that could potentially perforate and damage the tissues. By virtue of its nature and its shape, the frame only has rounded and atraumatic outer contours.

In particular, the frame 3 has a structure, in other words a shape, and a nature, in other words a material, giving it an elasticity such that it is able to adopt a first, unstressed configuration in which its shape follows substantially the contour of the peripheral outer edge and in which the textile 2 and the prosthesis 1 are deployed and spread out as shown in FIG. 1, and a second, stressed configuration in which its two long sides 3b are brought towards the central longitudinal axis of the textile 2, as shown in FIG. 2, and the prosthesis 1 has a compact shape in its radial direction.

Thus, in the example shown in FIG. 1, the frame 3, in its unstressed configuration, has substantially the shape of an ellipse, with two opposite long sides 3b, which are substantially parallel to the longitudinal axis A, and two opposite short sides 3c, which are substantially perpendicular to the longitudinal axis A. In the area of each of its short sides 3c, the frame 3 forms a U-shaped bend 4 extending, in the direction of the longitudinal axis A, towards the outside of the frame 3. Thus, the frame 3 follows substantially the outer edge of the textile, being slightly set back from this edge.

Alternatively, in an embodiment not shown, in which the textile has a rectangular shape with two opposite long sides and two opposite short sides, the shape of the frame follows the contour of the outer edge of the textile and likewise describes a rectangle with two opposite long sides and two opposite short sides, each of its opposite short sides being provided with a bend extending towards the outside of the frame or alternatively towards the inside of the frame.

On account of the nature and the structure of the frame 3, the U-shaped bends 4 act as guides for introducing the prosthesis 1 into a small orifice, such as an admission orifice of a trocar, when the frame 3 is in its stressed configuration. Indeed, when the user, for example using his hand, exerts a radial pressure on the opposite long sides of the frame 3 towards the longitudinal axis of the prosthesis 1, the resulting deformation of the frame 3 projects the U-shaped bends 4 towards the outside of the frame, as is shown in FIG. 3, the two opposite bends 4 remaining aligned on the longitudinal axis A.

Thus, in order to easily introduce the prosthesis 1 from FIG. 1 into a trocar, the user uses his hand 10 to exert the above-described radial pressure on the long sides 3b of the frame 3, as has been described with reference to FIG. 2, placing to the front, at each end of the prosthesis, the corresponding U-shaped bend 4. The prosthesis 1 then has a compact configuration in its radial part, substantially aligned on the longitudinal axis A of the textile 2 which forms at least one longitudinal fold. Depending on how the prosthesis 1 is folded and/or on the degree of stress applied to the frame 3, the textile 2 can form several longitudinal folds, like an accordion.

The user then takes hold of a trocar 5 into which he wishes to introduce the prosthesis 1. He brings the U-shaped bend 4, situated in the distal position and forming a guide element, towards the proximal orifice 5a of the trocar 5 and introduces it into the trocar 5. By virtue of its structure and its nature, the U-shaped bend 4 is sufficiently rigid to easily enter the conduit of the trocar 5 and to continue advancing under the effect of a distal push exerted by the user, as is shown in FIG. 3.

By virtue of its elongate compact shape, and the rigidity conferred on it by the presence of the frame 3, the prosthesis 1 also easily enters the conduit of the trocar 5, until the first U-shaped bend 4 of the frame 3 appears through the distal orifice 5b of the trocar, bringing with it the textile 2 to which it is connected, as is shown in FIG. 4.

The user continues to exert a distal push on the prosthesis 1, in particular on the frame 3 and on the proximally situated U-shaped bend 4 thereof which stiffens the prosthesis 1. As is shown in FIG. 5, as a larger part of the textile 2 of the prosthesis 1 gradually escapes from the stresses of the walls of the trocar 5, the frame 3 returns little by little to its initial state of rest and causes the automatic deployment of the textile 2 and, therefore, of the prosthesis 1. When the prosthesis 1 has emerged almost completely from the trocar 5, as is shown in FIG. 6, the frame 3 has practically recovered its ellipse shape corresponding to its unstressed configuration, and the textile 2 and therefore the prosthesis 1 are perfectly deployed and spread out.

The prosthesis 1 is then ready to be positioned opposite a hernia defect to be treated, without any risk of folds forming in the textile 2. The risks of adherence or insertion of surrounding organs in such folds are thus very much limited.

FIG. 7 shows another embodiment of the prosthesis 1 according to the invention, in which the textile 2 and the frame 3 also generally have the shape of an ellipse. However, in the example shown in this figure, the frame 3 forms a bend 6 which, in the direction of the longitudinal axis A, extends towards the inside of the frame 3, in the area of each of the short sides 3c thereof. Moreover, in the area of each of its long sides 3b, the frame 3 forms a supplementary bend 8, which extends towards the inside of the frame 3 in a direction perpendicular to the longitudinal axis A.

The presence of the bends 6 and of the supplementary bends 8 gives the frame 3 increased elasticity in the direction perpendicular to the longitudinal axis A. Such a shape of the frame 3 makes it possible to easily press the prosthesis 1 together and align it on the longitudinal axis A in the stressed configuration of the frame 3. Since the bends 6 on the short sides 3c extend towards the inside of the frame 3, the step of pressing together causes the formation of two stubs 7 on the frame 3 at each end of the prosthesis 1, these two stubs 7 acting as guide elements for the prosthesis 1 and making it easier to introduce the latter into the trocar, as has been explained above for the embodiment in FIG. 1.

The prosthesis according to the invention can thus be easily introduced into a trocar, without requiring the help of an additional tool, and without any risk of forming a plug inside the trocar. By virtue of its nature and its structure, the frame of the prosthesis according to the invention acts as a reinforcing element for the textile and stiffens the prosthesis, as an element for guiding and transporting the prosthesis inside a trocar conduit of particularly small diameter, such as a diameter of 5-15 mm, and also as a tool for assisting in the automatic and perfect spreading-out of the prosthesis at the moment when the latter emerges from the trocar at the implantation site.

The invention claimed is:

1. A prosthesis comprising:
    at least one flexible biocompatible textile of generally elongate shape defining a longitudinal axis, the textile being delimited by a peripheral outer edge forming substantially two opposite long sides and first and second opposite short sides, and
    at least one reinforcing element for the textile, wherein the reinforcing element is in the form of a resilient frame connected to the textile along substantially the peripheral outer edge of the long sides of the textile, the frame being set back from the peripheral outer edge and including a proximal U-shaped bend being convex to the peripheral outer edge of the first short side of the textile and a distal U-shaped bend being convex to the peripheral outer edge of the second short side of the textile, the proximal and distal U-shaped bends extending along a central longitudinal axis of the textile, the frame being able to adopt an unstressed configuration, in which the textile is deployed, and a stressed configuration, in which the frame is subjected to a radial force directed towards the longitudinal axis, the textile forms at least one longitudinal fold, and each of the proximal and distal U-shaped bends form a loop along the central longitudinal axis, the loop of the distal U-shaped bend forming a hard point configured to facilitate introduction of the prosthesis into a trocar and the loop of the proximal U-shaped bend forming a hard point configured to facilitate advancement of the prosthesis through a distal orifice of the trocar.

2. The prosthesis according to claim 1, wherein the frame is continuous.

3. The prosthesis according to claim 1, wherein the reinforcing element is molded over the textile.

4. The prosthesis according to claim 1, wherein the reinforcing element comprises a bioresorbable material.

5. The prosthesis according to claim 4, wherein the bioresorbable material is selected from the group consisting of polylactic acid, polycaprolactone, polydioxanones, trimethylene carbonates, polyvinyl alcohols, polyhydroxyalkanoates, oxidized cellulose, polyglycolic acid, and mixtures thereof.

6. The prosthesis according to claim 1, wherein the reinforcing element comprises a non-bioresorbable material.

7. The prosthesis according to claim 6, wherein the non-bioresorbable material is selected from the group consisting of polypropylenes, polyethylene terephthalates, polyamides, silicones, polyether ether ketones, polyarylether ether ketone, polyurethanes, and mixtures thereof.

8. The prosthesis according to claim 1, wherein the reinforcing element comprises a copolymer of polylactic acid and polyglycolic acid.

9. The prosthesis according to claim 1, wherein the reinforcing element comprises rounded and atraumatic outer contours.

10. The prosthesis according to claim 1, wherein the generally elongate shape is a rectangle.

11. The prosthesis according to claim 1, wherein the generally elongate shape is an ellipse.

12. The prosthesis according to claim 1, wherein the biocompatible textile is a two-dimensional knit mesh.

13. The prosthesis according to claim 1, wherein the biocompatible textile is a three-dimensional knit mesh.

14. The prosthesis according to claim 1, wherein one face of the biocompatible textile comprises a non-stick coating.

15. The prosthesis according to claim 1, wherein the frame is substantially parallel to the peripheral outer edge along the long sides.

16. The prosthesis according to claim 1, wherein the U-shaped bend is concave to a center of the textile.

17. A method of conveying a prosthesis to an implantation site comprising:
    providing a prosthesis including at least one flexible biocompatible textile of generally elongate shape defining a medial longitudinal axis, the textile being delimited by a peripheral outer edge forming substantially two opposite long sides and first and second opposite short sides, and at least one reinforcing element for the textile, wherein the reinforcing element is in the form of a resilient frame connected to the textile along substantially the peripheral outer edge of the long sides of the textile, the frame being set back from the peripheral outer edge and including a proximal U-shaped bend being convex to the peripheral outer edge of the first short side of the textile, and a distal U-shaped bend being convex to the peripheral outer edge of the second short side of the textile, the proximal and distal U-shaped bends extending along the medial longitudinal axis of the textile,
    folding the two opposite long sides of the textile over the medial longitudinal axis via the proximal and distal U-shaped bends to place the textile in a stressed configuration, each of the proximal and distal U-shaped bends forming a loop along the medial longitudinal axis, the loop of the distal U-shaped bend forming a hard point configured to facilitate introduction of the prosthesis into a trocar and the loop of the proximal U-shaped bend forming a hard point configured to facilitate advancement of the prosthesis through a distal orifice of the trocar,
    introducing the textile in the stressed configuration into a proximal orifice of a trocar via the hard point formed by the loop of the distal U-shaped bend, and
    advancing the textile via the hard point of the proximal U-shaped bend through a distal orifice of the trocar to the site of implantation wherein the textile automatically unfolds from the stressed configuration to an unstressed configuration.

18. A prosthesis comprising:
- a flexible biocompatible textile of an elliptical shape defining a central longitudinal axis, the textile being delimited by a peripheral outer edge, and
- a reinforcing element in the form of a resilient frame connected to the textile, the frame including a first long side having a proximal and distal end, a second long side having a proximal and distal end, the first and second long sides positioned on opposite sides of the central longitudinal axis and defining a generally elliptical shape, a first U-shaped bend connected to the proximal ends of the first and second long sides of the frame and extending along the central longitudinal axis away from the proximal ends of the first and second long sides of the frame, and a second U-shaped bend connected to the distal ends of the first and second long sides of the frame and extending along the central longitudinal axis away from the distal ends of the first and second long sides of the frame, the first and second U-shaped bends each being convex to the peripheral outer edge of the textile.

19. The prosthesis of claim 18, wherein the first and second U-shaped bends are closer to the peripheral outer edge of the textile than the proximal and distal ends of the first and second long sides of the frame.

20. The prosthesis of claim 19, wherein the frame is able to adopt an unstressed configuration, in which the textile is deployed, and a stressed configuration, in which the frame is subjected to a radial force directed towards the central longitudinal axis and each of the first and second U-shaped bends form a hard point acting as a guide element along the central longitudinal axis to facilitate introduction of the prosthesis into a trocar and advancement of the prosthesis through the trocar to a site of implantation.

* * * * *